United States Patent [19]
Stahl et al.

[11] Patent Number: 5,098,836
[45] Date of Patent: Mar. 24, 1992

[54] DEOXYGENATION IN FIELD PREPARATION OF POLYMERS IN AQUEOUS SOLUTION

[75] Inventors: G. Allan Stahl, Humble, Tex.; Thomas R. Hopkins, Bartlesville, Okla.

[73] Assignee: Phillips Petroleum Company, Bartlesville, Okla.

[21] Appl. No.: 393,161

[22] Filed: Aug. 14, 1989

[51] Int. Cl.$^5$ .................. C12P 17/10; C12P 17/18; C12P 13/00; C12P 13/02
[52] U.S. Cl. .................................. 435/121; 435/119; 435/122; 435/128; 435/189; 435/190; 435/191
[58] Field of Search ............. 435/121, 128, 119, 122, 435/190, 191, 189

[56] References Cited

U.S. PATENT DOCUMENTS

| | | | |
|---|---|---|---|
| Re. 23,523 | 7/1952 | Baker | 99/48 |
| 3,500,925 | 3/1970 | Beiswanger et al. | |
| 3,733,205 | 5/1973 | Shovers et al. | 99/48 |
| 3,788,950 | 1/1974 | Hicks et al. | |
| 4,395,340 | 7/1983 | McLaughlin | 252/8.55 D |
| 4,414,334 | 11/1983 | Hitzman | 435/262 |

OTHER PUBLICATIONS

JPO Abstract 57-32213, Yoshida et al, Jun. 11, 1982.

*Primary Examiner*—Herbert J. Lilling
*Attorney, Agent, or Firm*—J. E. Phillips

[57] ABSTRACT

In a process for polymerizing monomers with free-radical initiators in aqueous solution to produce polymers useful in oil field applications, wherein said polymerization process employs an oxygen-scavenging agent, the improvement which comprises employing said oxygen scavenging agent and oxidase enzyme with a substrate therefor, optionally with a catalase, such as alcohol oxidase and methanol, to consume dissolved oxygen in a polymerization admixture. Oxygen-scavenging under field conditions with the oxidase/substrate system permits consistent production conveniently of water based polymer solutions of good viscosity for oil field applications.

11 Claims, No Drawings

DEOXYGENATION IN FIELD PREPARATION OF POLYMERS IN AQUEOUS SOLUTION

FIELD OF THE INVENTION

The invention pertains to methods for the field preparation (polymerization) of water soluble/dispersible polymers. In another aspect, the invention pertains to methods for the elimination of dissolved oxygen in field location aqueous polymerization procedures. In a further aspect, the invention pertains to methods to prepare aqueous solutions/dispersions of polymers for injection into underground strata in hydrocarbon-bearing formations.

BACKGROUND OF THE INVENTION

Aqueous polymer solutions/dispersions are effective to enhance the production of hydrocarbons, particularly crude oil, from subterranean hydrocarbon-containing formations. The aqueous polymer solutions/dispersions are used for a variety of purposes, such as contrast correction of heterogeneous subterranean formations, and in polymerflooding. In polymerflooding the polymers are introduced as aqueous solutions/dispersions into a formation through one well bore to endeavor to flush or drive oil remaining in the formation toward a production area. A variety of water-soluble polymers have been employed, including polymers which have been prepared from polymerizable vinyl monomers, such as the acrylamide, alone, or copolymers of various monomers copolymerizable therewith. The polymers are diluted to produce polymer solutions of various viscosities depending on the desired treatment approach.

Generally, the water-soluble organic polymers have been produced as either a dry, semi-dry (powdered, granular, or briquette form) or liquid concentrate for economic shipment to the site of use.

In the manufacture of the polymers in solid form, the monomers are typically polymerized in water, and the resulting polymer then is dewatered for formation into a solid suitable for shipping purposes. The conditions of removal of the water often cause undesirable crosslinking of the polymer chains, resulting in a highly heterogenous molecular distribution. The crosslinked polymers form insoluble gel domains, called micro-gels, that may swell without dissolving when later contacted with water in efforts to re-dissolve the polymers to form a solution. The resultant undissolved micro-gel particles tend to plug the formation into which they are ultimately injected. Some of these partially crosslinked materials also may be incompatible with some connate waters.

Producing a powdered or particulate form of polymer generally also has involved some type of grinding process. This causes some degree of degradation of the polymer by shearing of long polymer chains whereby the molecular weights thereof are reduced, resulting in a product of highly variable and uncertain molecular weight, affecting radically suitability, solubility, and results.

Accurate control of the product and results to be obtained therefrom becomes very difficult.

The dry polymers must be dissolved or dispersed in aqueous treating or injection solutions at the site, either continuously or on a periodic batch basis. Unfortunately, the dissolution of solid organic polymers in aqueous solutions frequently is difficult, time consuming, and may require special mixing equipment.

Many of the difficulties encountered with dry and semi-dry polymers may be alleviated by utilizing a preparation of water-soluble organic polymers in a liquid emulsion concentrate. The liquid emulsion concentrate usually consists of 20-30 percent active polymer solution in the internal or "water" phase of the emulsion with oil constituting the continuous phase. Since the active polymer is in the internal or water phase, the liquid concentrate has a relatively low viscosity. To render the active polymer suitable for subterranean use, water must be mixed with the liquid emulsion concentrate utilizing special turbulent mixing equipment.

Although liquid emulsion concentrates are easy to make and ship, several disadvantages are inherent with their use. Because the liquid emulsion concentrate must be shipped as an emulsion, the concentration of polymer in the emulsion is limited. Additionally, the ultimate viscosity of the aqueous solution can be expected to be lower due to the degradation of the polymers which occur during turbulent mixing of the liquid emulsion concentrate. Moreover, once the liquid concentrate has been converted to an aqueous solution, utilizing this concentrated polymer and water solution presents several difficulties due to the solution's high viscosity, such a high well-head pressures, polymer shearing during injection, and formation fracturing which may occur as the solution is injected.

One answer to these difficulties encountered with dry, semi-dry, and liquid concentrate of polymer has been to polymerize the monomers in the field, at the well site, as suggested in U.S. Pat. No. 4,395,340 (McLaughlin, July 26, 1983). According to McLaughlin, the formation of the polymers in an aqueous solution at or near the subterranean location of their use avoids the problems mentioned above relating to the use of solid-form polymers, and also avoids the extra expenses associated with producing polymers in solid form in a factory, shipping, and subsequently at the job site having to redissolve the polymers to make the aqueous injection solution/dispersion.

In the preparation of water-soluble polymers, it is known that oxygen must be eliminated from the reactants and from the water employed as polymerization solvent. The presence of dissolved oxygen in the aqueous medium in which the vinyl monomers are to be polymerized either prevents the polymerization reaction from taking place or interferes with the reaction so that long-chain, high molecular weight polymers are not formed. In normal manufacturing processes, a nitrogen or argon purge is recommended to displace the oxygen from the monomers and water.

The McLaughlin patent suggests that for on-site preparation of polymer solutions wherein one or more vinyl monomers are polymerized in an aqueous solvent that dissolved oxygen be preferably removed by purging the solvent with an inert gas. While this remains the method of choice, treatment with inert gas is not practical and is not reasonably avaiable for field-site usage. As an alternative to inert gas usage, McLaughlin suggests that sulfite or related inorganic sulfur-based oxygen scavengers, such as the bisulfites, pyrosulfites, and the like, are effective in avoiding this problem.

However, according to our investigations, sulfite and related types of oxygen scavenging agents are not suitable. This is believed to be due to the slow reactivity of sulfite ion with the propagating polymer free radical.

This reaction transfers the free radical from the polymer to the medium thus limiting the molecular weight of the polymer. Furthermore the inorganic radical so produced can react with the polymer causing chain sission and a decrease in the molecular weight of the polymer. Whatever the explanation, the use of the sulfite-type inorganic chemical oxygen scavengers produces highly erratic polymeric products as to consistent quality, relative viscosity, inherent viscosity, and dependability.

A method is needed for the elimination of oxygen from polymerization reaction mixtures in field polymerization procedures. The method should be easy and simple to use, highly effective under normal conditions, consistent in its results, and not deleterious to the polymers long term stability.

BRIEF DESCRIPTION OF THE INVENTION

We have discovered that the use of an oxygen scavenging system comprising an oxidoreductose enzyme, and molecular oxygen when reacted with at least one substrate, and optionally, with a co-enzyme, effectively removes dissolved oxygen, and enables production of aqueous polymer solutions of high viscosity on a consistent and uniform basis.

In accordance with our process, an oxygen scavenging system is added in amounts sufficient to substantially eliminate dissolved oxygen from the water used as polymerization solvent. This oxygen scavenging system can be added to the water prior to the addition of the monomers, or the monomers and water can be prepared as an admixture, with the oxygen scavenging system added thereto, followed by the addition of a suitable free radical initiator to polymerize the monomers, and resulting in the desired aqueous solution of polymer.

Our process is highly effective for consistent polymerizing of monomers with free radical initiators to produce aqueous polymer solutions of high viscosity useful in oil field applications.

Enzymes

The particular primary enzyme chosen is required to be an oxidoreductase. Examples of suitable oxidoreductase enzymes include oxidases, monooxygenases, hydroxygenases, hydrolases, and oxygenases. Oxidoreductase enzymes act as catalysts, and in the presence of a substrate and dissolved molecular oxygen catalizes the oxidation of the substrate and reduction of the molecular oxygen. In some of these reactions, a side product of this reaction is hydrogen peroxide which may inactivate the oxidoreductase enzyme used. To remove hydrogen peroxide, a catalase enzyme may be employed to breakdown hydrogen peroxide.

The oxidoreductase enzyme will react with the substrate until substantially all the substrate is oxidized or all the available molecular oxygen is reduced. Thus, the concentration of molecular oxygen will be diminished as the substrate and molecular oxygen are reacted together by the oxidoreductase enzyme and the concentration of molecular oxygen will become substantially zero where an excess of concentration substrate is present, in accordance with the following reactions (where $RH_2$ is the substrate and R is the oxidized substrate)

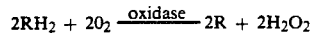

$$2RH_2 + 2O_2 \xrightarrow{\text{oxidase}} 2R + 2H_2O_2$$

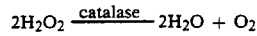

$$2H_2O_2 \xrightarrow{\text{catalase}} 2H_2O + O_2$$

-continued

$$\text{Net: } 2RH_2 + O_2 \longrightarrow 2R + 2H_2O$$

While $O_2$ removal can be performed using pure enzymes and pure substrate, our method works equally well using impure preparations of enzyme and substrate, thus saving considerable materials cost. Many impure oxidases also have appreciable amount of catalase present, thus automatically providing the optional second enzyme which can be used in our oxygen scavenging system.

Additionally, hydrogen peroxide is itself an initiator of polymerization of acrylamide and related monomers. Under certain circumstances, it would be desirable to use the hydrogen peroxide produced from the oxidase-catalyzed reaction of oxygen and a substrate to initiate or augment other additives designed to initiate the polymerization of monomers.

Any suitable and effective oxidase/substrate pair can be employed. The following table lists exemplary oxidase/substrate couples or pairs that can be employed in the process of the present invention:

TABLE I

| | Oxidase | Substrate |
|---|---|---|
| 1. | phenol oxidase | phenols and catechols |
| 2. | aldehyde oxidase | aldehydes and purines |
| 3. | amino acid oxidase | amino acids |
| 4. | uricase | uric acid |
| 5. | glucose oxidase | glucose |
| 6. | amine oxidase | mono- and diamines |
| 7. | lipoxygenase | unsaturated fatty acids |
| 8. | ascorbic oxidase | vitamin C (ascorbic acid) |
| 9. | alcohol oxidase | ethyl alcohol |
| 10. | alcohol oxidase | methyl alcohol |
| 11. | methane monooxygenase | methane |

The amounts of oxidase and substrate of the oxygen scavenging system to be employed will depend on the specific activity of the enzyme, how quickly the reaction is desired to go to completion, and the amount of molecular oxygen which must be removed. The amounts of oxidase and substrate to be employed will be determined on a case by case basis and can be determined by those skilled in the art. It is preferable to employ somewhat greater than the minimum amounts of substrate, in order to allow for any in leakage of oxygen from external sources, and the like.

It also is considered desirable to employ an excess amount of the oxygen scavenging system to provide continuing protection for the resulting aqueous polymer solution against degradation from possible further contact with molecular oxygen prior to its use.

Treating Procedure

In general, it presently is considered preferable to admix the oxidoreductase, the suitable substrate and, where needed, a catalase enzyme, with the volume of water to be deoxygenated. Thereafter, the monomers are added, followed by the polymerization initiator to commence polymerization.

If desired, the monomers together with the water as solvent, can be formed into an admixture, and the entire body then deoxygenated. Thereafter, the free radical initiator can be added to commence polymerization.

In another mode, the aqueous polymerization components, including monomer(s), water, and initiators, can be admixed, our oxygen-scavenging system then added thereto, and polymerization allowed to commence and continue to substantial completion.

The product of the process of the present invention is a stable aqueous solution/dispersion of the desired polymer. No recovery procedures are required. The aqueous solution of polymer can be further diluted with water, if desired, for injection purposes depending on the particular oil field purpose and need. For some purposes, the polymerization solution as prepared can be used directly for injection purposes.

Polymers

Our process is applicable to the aqueous media polymerization of one or more vinyl-containing monomers polymerizable under aqueous polymerization conditions employing free radical initiators in which the deoxygenation of the aqueous admixture is desirable. Such polymerization processes need not be repeated here. Among the preferred polymers for use in the practice of the present invention are the acrylamide based polymers. These polymers include the homopolymer polyacrylamide, as well as the thermally stable copolymers of acrylamide with monomers copolymerizable therewith, such as N-vinylpyrrolidone, acrylic acid (and its salts), sodium (or other alkali metal)-2-acrylamido-2-methyl-1-propanesulfonate, alone, or in various combinations.

Among the presently preferred polymers are copolymers of: acrylamide and N-vinylpyrrolidone; acrylamide/N-vinylpyrrolidone/sodium-2-acrylamido-2-methyl-1-propanesulfonate; acrylamide/N-vinylpyrrolidone/sodium-2-acrylamido-2-methyl-1-propanesulfonate/acrylic acid; and acrylamide/N-vinylpyrrolidone/sodium-2-acrylamido-2-methyl-1-propanesulfonate/sodium acrylate. These copolymers frequently are made with lesser amounts of copolymerized monomeric such as vinyl acetate, vinypyridine, styrene, methyl methacrylate, and the like.

In general, the aqueous solvent is deoxygenated, and the vinyl-containing monomer(s) admixed therewith. Alternatively, the vinyl-containing monomers can be admixed with the water/solvent and the deoxygenation system added thereto. Thereafter, a free radical polymerization initiator is added to bring about the rapid polymerization of the monomer(s), or the water, monomer(s), and initiator can be admixed and the deoxygenation system thereafter added.

Various free-radical initiators are known in the art. Initiators suitable for use in the practice of the present invention include, but are not limited to, 2,2'-azobisisobutyronitrile, 2,2'-azobis(2,4-dimethylvaleronitrile), 2,2'-azobis(2,4-dimethyl-4-methoxyvaleronitrile), 2,2'-azobis(2-amidimopropane)hydrochloride, and 2,2'-azobis(N,N'-dimethyleneisobutyramidine)dichloride. In the systems employing our invention, the persulfates and peroxides are to be avoided.

The polymeric product of the present invention is advantageous as an aqueous polymeric solution to be utilized in the treatment of subterranean oil-bearing formations. The polymeric products are not cross-linked, do not contain micro-gels, and have uniform desirable molecular weights.

Where desired, the pH can be adjusted, and amide groups of the polymers can be hydrolyzed to carboxylate groups which are advantageous in some applications, depending on the cation content of the water used for polymerflood purposes, as is known in the art.

EXAMPLE I

Acrylamide (AM) and N-vinylpyrrolidone (VP) were copolymerized in a series of runs employing a weight ratio of 40:60 AM:VP, deoxygenating with an enzyme system (alcohol oxidase, methanol), and employing an azo compound as polymerization initiator (AI).

In general, in each run a closed reactor was charged with indicated amounts of monomers, initiator and water. The water was in the form of synthetic North Sea water (SNSW) produced as set forth in footnote (c) in Table I-1. Control Runs 1 and 2 employing nitrogen were degassed for about 20 minutes by bubbling nitrogen through the admixture. In Inventive Runs 3-8 employing the oxygen scavenging system, the admixture was not deoxygenated, but the air space was purged with nitrogen in order to provide uniformity of results for comparative purposes. Polymerizations were conducted at room temperature since the initiator is active at that temperature. TABLE I-1 sets forth the identity and amounts of reagents employed in Runs 1-8 of Example I.

The dissolved oxygen (DO) content was measured on Samples of Runs 2, 4, 6, and 8 after about 20 minutes of deoxygenation treatment, and the results are set forth in TABLE I-2.

TABLE I-2

| Dissolved Oxygen Content[a] | |
|---|---|
| Run | DO - ppm |
| 2 | 0 |
| 4 | <1 |
| 6 | <1 |
| 8 | <1 |

[a]The assay was performed with a commercially available dissolved oxygen kit which compares the color developed in the unknown mix against colors of mixtures of known, $O_2$ content.

After polymerization appeared to be complete, a 0.25 percent by weight polymer solution was made from each sample (SNSW was used as the diluent) and treated at 50° C. in a water bath for 24 hours to assure complete solution mixing. Samples were afterward removed and Brookfield viscosities (spindle UL, 6 rpm) were measured at 25° C. after 2 minutes, and after 12 minutes, and the results are set forth in TABLE I-3.

TABLE I-1

| Run No. | VP g[a] | AM g | AI g[b] | Water g[c] | Enzyme μL[d][e] | Methanol μL | Degasification[f] |
|---|---|---|---|---|---|---|---|
| 1 | 26.4 | 17.6 | 0.44 | 176 | — | — | Nitrogen |
| 2 | 26.4 | 17.6 | 0.44 | 176 | — | — | Nitrogen |
| 3 | 26.4 | 17.6 | 0.44 | 176 | 25 | 25 | — |
| 4 | 26.4 | 17.6 | 0.44 | 176 | 25 | 25 | — |
| 5 | 26.4 | 17.6 | 0.44 | 176 | 25 | 100 | — |
| 6 | 26.4 | 17.6 | 0.44 | 176 | 25 | 100 | — |
| 7 | 26.4 | 17.6 | 0.44 | 176 | 25 | 250 | — |

TABLE I-1-continued

| Run No. | VP g[a] | AM g | AI g[b] | Water g[c] | Enzyme μL[d][e] | Methanol μL | Degasification[f] |
|---|---|---|---|---|---|---|---|
| 8 | 26.4 | 17.6 | 0.44 | 176 | 25 | 250 | — |

[a] g = grams
[b] AI = Azo Initiator. Employed was 2,2'-azobis(2,4-dimethyl-4-methoxyvaleronitrite) as a 0.10 wt. % solution in water.
[c] Synthetic North Sea Water (SNSW) made by dissolving 3.69 g NaHCO$_3$, 77.19 g Na$_2$SO$_4$, 429.00 g NaCL, 29.58 g CaCl$_2$.2H$_2$O, and 193.92 g MgCl$_2$.6H$_2$O to 18.0 liter volume mark with distilled water.
[d] Enzyme employed was alcohol oxidase at a indicate concentration of 1000 Eu/ml.
[e] μL = microliters.
[f] By bubbling the gas through the reactor contents. Samples not degassed were "capped" to have an oxygen-free head space.

TABLE I-3

| Run No. | Brookfield Viscosity, cp | |
|---|---|---|
| | @ 2 minutes | @ 12 minutes |
| 1 | 4.9 | 4.7 |
| 2 | 5.3 | 5.4 |
| 3 | 4.0 | 4.9 |
| 4 | 5.4 | 5.4 |
| 5 | 5.7 | 5.5 |
| 6 | 5.8 | 5.8 |
| 7 | 5.4 | 5.2 |
| 8 | 5.1 | 5.0 |

The results clearly show that our oxygen scavenging system permits production of polymers (Runs 3-8) at least as high in viscosity as those obtained with nitrogen stripping of the solution (Runs 1 and 2).

EXAMPLE II

Runs were made to determine the effect of alcohol oxidase/ethanol in an oxygen scavenging system in a polymerization of 40:60 wt. ratio acrylamide:N-vinylpyrrolidone. Since Runs 5 and 6 of Example I indicated that a level of about 100 μL of methanol per 220 g solution was effective in the removal of dissolved oxygen, this amount of ethanol was used in all inventive Runs of this Example II, while varying the enzyme level.

Charge order: The monomers and water were admixed and charged to a closed reactor. Control samples were degassed in the reactor (Runs 9-12) as described in Example I; and the oxygen scavenging system was added to the reactor as indicated to the inventive Runs (13-18). The reactor was closed and polymerization proceeded at room temperature. The azo initiator was added to the reactor immediately prior to the oxygen scavenging system in Runs 13-18.

Degassing of Runs 9-12 continued for 20 minutes. The enzyme system was added to Runs 13-18 at the same time as degassing began in Runs 9-12. In Runs 13-18 the air space in the reactor above the reagents was exchanged with argon prior to closing the reactor.

Observation were made of when polymerization started. TABLE II-1 sets forth the identity and amounts of reagents employed and the results obtained in Runs 9-18.

After polymerization, a portion of the reaction product of each of Runs 9-18 was diluted to 0.25 weight percent polymer solution with SNSW and treated in a water bath at 50° C. to assure adequate solution as described in previous Example I. Thereafter, Brookfield viscosities at two minutes and 12 minutes were measured for each diluted sample. Results obtained at two minutes and 12 minutes under conditions used in Example I are shown in TABLE II-2.

TABLE II-2

| Run No. | Brookfield Viscosity, cp | |
|---|---|---|
| | After 2 Minutes | After 12 Minutes |
| 9 | 6.8 | 6.3 |
| 10 | 5.4 | 5.5 |
| 11 | 3.7 | 3.9 |
| 12 | 5.8 | 5.5 |
| 13 | 4.1 | 4.1 |
| 14 | 4.2 | 4.1 |
| 15 | 5.0 | 4.9 |
| 16 | 4.7 | 4.6 |
| 17 | 4.0 | 3.9 |
| 18 | 5.7 | 5.6 |

TABLE II-1

| Run No. | VP g | AM g | AI g[a] | Water g[b] | Oxidase μl[c] | Ethanol μl | Degassing[d] | Dissolved Oxygen Content After 70 Min. | Time for Polymerization to Start[e] |
|---|---|---|---|---|---|---|---|---|---|
| 9 | 26.4 | 17.6 | 0.05 | 176 | — | — | Argon | 0 | Immediately |
| 10 | 26.4 | 17.6 | 0.05 | 176 | — | — | Argon | 0 | Immediately |
| 11 | 26.4 | 17.6 | 0.05 | 176 | — | — | Nitrogen | 0 | Immediately |
| 12 | 26.4 | 17.6 | 0.05 | 176 | — | — | Nitrogen | 0 | Immediately |
| 13 | 26.4 | 17.6 | 0.05 | 176 | 10 | 100 | — | — | — |
| 14 | 26.4 | 17.6 | 0.05 | 176 | 10 | 100 | — | 1.5 ppm | — |
| 15 | 26.4 | 17.6 | 0.05 | 176 | 25 | 100 | — | — | — |
| 16 | 27.4 | 17.6 | 0.05 | 176 | 25 | 100 | — | 1 ppm | — |
| 17 | 26.4 | 17.6 | 0.05 | 176 | 50 | 100 | — | — | After 4 hours |
| 18 | 26.4 | 17.6 | 0.05 | 176 | 50 | 100 | — | <1 ppm | After 3 hours |

[a] Same initiator solution as in Example I.
[b] SNSW described above.
[c] Alcohol oxidase derived from the yeast, Pichia pastoris (Provesta Corporation, Bartlesville, OK)
[d] By bubbling the gas through the reactor contents. Samples not degassed were "capped" with argon to have an oxygen-free head space.
[e] Runs 13-16 had started to polymerize after 4 hours.

The data indicate, in general, that results from the use of the oxidase oxygen scavenging system of the present invention are substantially as good as those obtained in the use of inert gas purging.

EXAMPLE III

Further runs were made to evaluate the effects of an oxygen scavenging system employing an alcohol oxidase with ethanol as substrate, on dissolved oxygen and on the effects on the copolymerization of acrylamide (AM) and N-vinylpyrrolidone (VP) (40/60). The system was substantially handled in a manner similar to that described in the previous Example II. The reagents were charged to a closed reactor, and those samples not employing our oxygen scavenging system were degassed (Runs 19-22), while those systems employing the oxygen scavenging system were treated with the oxidase and substrate (Runs 23-28) at the same time as the other samples commenced their degassing. The azo initiator was added immediately prior to the addition of the oxidase/substrate system additions. All reactors were closed, those samples using the enzyme/substrate (Runs 23-28) were capped with argon and polymerization times noted. TABLE III-1 sets forth the identity and amounts of reagents employed and the results obtained in Runs 19-28 of Example III.

After polymerization was complete, dilutions to 0.25 percent by weight polymer with SNSW were made on a portion of the reactive product of each of Runs 19-28, and the diluted reaction product samples were placed in a 50° C. water bath overnight for thorough solution.

TABLE III-2-continued

| | Brookfield Viscosity, cp | |
|---|---|---|
| Run No. | Two Minutes | 12 Minutes |
| 27 | 5.5 | 5.4 |
| 28 | 5.6 | 5.6 |

Results in these Runs show that the inventive oxygen scavenging system (Runs 23-28 inclusive) produced polymers of slightly lower viscosities than the polymers obtained in Runs 19-22 using the degasifying procedures. However, polymerizations with the oxygen scavenging system produced good polymers of generally uniform, consistent, and satisfactory character.

EXAMPLE IV

Further Runs 29-38 were made employing a 40:60 weight ratio acrylamide:N-vinylpyrrolidone aqueous copolymerization, similar to that described in the previous Examples. However, in these Runs, a different enzyme/substrate was employed in the oxygen scavenging system. Glucose oxidase and glucose were used as

TABLE III-1

| Sample | VP g | AM g | AI g[a] | Water g[b] | Oxidase μL[c] | Ethanol μL | Degasification[d] | Polymerization Commenced |
|---|---|---|---|---|---|---|---|---|
| 19 | 26.4 | 17.6 | 0.05 | 176 | — | — | Argon | within 2 hours |
| 20 | 26.4 | 17.6 | 0.05 | 176 | — | — | Argon | within 2 hours |
| 21 | 26.4 | 17.6 | 0.05 | 176 | — | — | Nitrogen | within 2 hours |
| 22 | 26.4 | 17.6 | 0.05 | 176 | ' | — | Nitrogen | within 2 hours |
| 23 | 26.4 | 17.6 | 0.05 | 176 | 100 | 100 | — | after 6 hours |
| 24 | 26.4 | 17.6 | 0.05 | 176 | 100 | 100 | — | after 6 hours |
| 25 | 26.4 | 17.6 | 0.05 | 176 | 50 | 100 | — | after 6 hours |
| 26 | 27.4 | 17.6 | 0.05 | 176 | 50 | 100 | — | after 6 hours |
| 27 | 26.4 | 17.6 | 0.05 | 176 | 25 | 100 | — | after 6 hours |
| 28 | 26.4 | 17.6 | 0.05 | 176 | 25 | 100 | — | after 6 hours |

[a]Same initiator solution as in Example I.
[b]SNSW, see Example I.
[c]Alcohol oxidase derived from the yeast *Pichia pastoris* (Provesta Corporation, Bartlesville, OK)
[d]By bubbling the gas through the reactor contents. Samples not degassed were "capped" with argon to have an oxygen-free head space.

Thereafter, Brookfield viscosities were measured as before at two minutes and at 12 minutes on each, and the results obtained are shown in TABLE III-2.

TABLE III-2

| | Brookfield Viscosity, cp | |
|---|---|---|
| Run No. | Two Minutes | 12 Minutes |
| 19 | 6.1 | 6.0 |
| 20 | 6.3 | 6.1 |
| 21 | 6.3 | 6.2 |
| 22 | 6.0 | 6.0 |
| 23 | 4.4 | 4.2 |
| 24 | 5.1 | 5.3 |
| 25 | 5.4 | 5.4 |
| 26 | 5.7 | 5.6 | the enzyme/substrate for oxygen scavenging rather than the previously used alcohol oxidase, and ethanol or methanol. The reagents were charged to a closed reactor, deoxygenated as indicated in TABLE IV-1, the reactors capped, and the contents allowed to polymerize at room temperature.

TABLE IV-1

| Run No. | VP g | AM g | AI g[a] | Water g[b] | Oxidase μL[c] | Glucose μL | Degassing[d] |
|---|---|---|---|---|---|---|---|
| 29 | 26.4 | 17.6 | 0.05 | 176 | — | 250 | Argon |
| 30 | 26.4 | 17.6 | 0.05 | 176 | — | 250 | Argon |
| 31 | 26.4 | 17.6 | 0.05 | 176 | — | 250 | Argon |
| 32 | 26.4 | 17.6 | 0.05 | 176 | — | 250 | Nitrogen |
| 33 | 26.4 | 17.6 | 0.05 | 176 | 25 | 250 | — |
| 34 | 26.4 | 17.6 | 0.05 | 176 | 25 | 250 | — |
| 35 | 26.4 | 17.6 | 0.05 | 176 | 10 | 250 | — |
| 36 | 26.4 | 17.6 | 0.05 | 176 | 10 | 250 | — |
| 37 | 26.4 | 17.6 | 0.05 | 176 | 250 | 250 | — |
| 38 | 26.4 | 17.6 | 0.05 | 176 | 250 | 250 | — |

[a]Same initiator solution as in Example I.
[b]SNSW. See Example I.
[c]Oxidase used with glucose oxidase derived from the fungus, *Aspergillus niger* (Sigma Chem. Co., St. Louis, MO)
[d]By bubbling the gas through the reactor contents. Samples not degassed were "capped" with argon so as to have an oxygen-free head space.

Again, in Runs 29-32, control samples were degassed employing argon or nitrogen for comparative purposes. In each of Runs 33-38 the azo initiator was added immediately prior to the glucose oxidase/glucose addition where employed. The reagents employed in Runs 29-38 and the amounts thereof are shown in TABLE IV-1.

Polymerization commenced substantially immediately in most of the runs of Example IV. Within 45 minutes, the reagents in Runs 29, 30, 31, 32, 37, and 38 had polymerized to a gel form. Runs 35 and 36 each took about two additional hours before polymerization initiated.

Brookfield viscosity measurements were not made on any of these preparations. Instead, samples of the reaction products of each of Runs 29-38 were prepared for relative and inherent viscosity measurements at 0.10 weight percent polymer in SNSW, with the results obtained being set forth in TABLE IV-2.

TABLE IV-2

| Sample No. | Relative Viscosity | Inherent Viscosity |
| --- | --- | --- |
| 29 | 2.04 | 7.13 |
| 30 | 1.87 | 6.24 |
| 31 | 2.06 | 7.24 |
| 32 | 2.03 | 7.07 |
| 33 | 1.91 | 6.46 |
| 34 | 2.09 | 7.35 |
| 35 | 1.92 | 6.52 |
| 36 | 1.93 | 6.57 |
| 37 | 1.81 | 5.96 |
| 38 | 2.01 | 7.01 |

Results set forth in TABLE IV-2 indicate that the glucose oxidase/glucose employed (Runs 33-38) as the oxygen scavenging system produced polymers generally equivalent to or at least as good as polymers produced employing the degasification procedures (Runs 29-32).

EXAMPLE V

Comparative Runs 39-41 were made to prepare polyacrylamide homopolymer (a) in water which was not deoxygenated (Run 39), (b) in water deoxygenated by argon-stripping (Run 40), and (c) in water deoxygenated with our inventive oxygen scavenging system using alcohol oxidase/ethanol system (Run 41).

The reagents were admixed as described before, with the argon stripped reagents of Run 40 being degassed for about 20 minutes. Alcohol oxidase and ethanol were added immediately prior to addition of the azo initiator in Run 41. Polymerization was permitted to continue overnight at room temperature in all three runs. TABLE V-1 sets forth the identity and amounts of reagents employed in Runs 39-41.

Run 39 took several days before the reagents polymerized. In Runs 40 and 41 the reagents polymerized overnight each producing a thick gel with some appearance of gas bubbles.

A portion of each polymer was examined for relative viscosity and inherent viscosity at 0.10 weight percent polymer in distilled water, with the results of such examinations being set forth in TABLE V-2.

TABLE V-2

| Run No. | Relative Viscosity | Inherent Viscosity |
| --- | --- | --- |
| 39 | 2.08 | 7.34 |

TABLE V-2-continued

| Run No. | Relative Viscosity | Inherent Viscosity |
| --- | --- | --- |
| 40 | 1.86 | 6.23 |
| 41 | 2.24 | 8.07 |

Run 39, which was not deoxygenated and took several days to polymerize, plainly would be impractical under field or commercial conditions.

TABLE V-1

| Run No. | AM g | Water g$^{(a)}$ | Al g$^{(b)}$ | Degasification$^{(c)}$ | Alcohol Oxidase μl$^{(d)}$ | Ethanol μl |
| --- | --- | --- | --- | --- | --- | --- |
| 39 | 20 | 180 | 0.04 | — | — | — |
| 40 | 20 | 180 | 0.04 | Argon | — | — |
| 41 | 20 | 180 | 0.04 | — | 25 | 100 |

$^{(a)}$Distilled water.
$^{(b)}$Same initiator as in Example I.
$^{(c)}$By bubbling the gas through the reactor contents. Samples not degassed were "capped" with argon so as to have an oxygen-free head space.
$^{(d)}$Alcohol oxidase derived from the yeast *Pichia pastoris* (Provesta Corporation, Bartlesville, OK).

Run 41, employing the inventive oxygen scavenging system produced polymer showing an improvement in inherent viscosity as opposed to the polymer resulting from Run 40 employing argon-stripping in this comparison.

EXAMPLE VI

Runs 42-44 were made to prepare a homopolymer of acrylic acid (AA) in water. Runs were made to compare results from no deoxygenation, versus argon-stripping, versus our inventive oxygen scavenging system. The reagents were charged as indicated below, deoxygenated as shown, and placed in closed containers to tumble overnight at about 50° C. polymerization temperature. Again, the initiator employed was added just prior to our oxygen scavenging system. TABLE VI-1 sets forth the identity and amounts of reagents employed in Runs 42-44:

After 24 hours, only Run 43 had polymerized. Run 44 did polymerize later, though slowly. Run 42, which was not deoxygenated by any manner, never did polymerize.

A small portion of each of the polymers of Runs 43 and 44 was tested for relative and inherent viscosity at 0.10 weight percent polymer in distilled water, with the results of such testing being set forth in TABLE VI-2.

TABLE VI-2

| Run No. | Relative Viscosity | Inherent Viscosity |
| --- | --- | --- |
| 43 | 4.02 | 13.93 |
| 44 | 3.64 | 12.33 |

Results show the importance of deoxygenating the aqueous polymerization system prior to initiation; and that the inventive oxygen scavenging system produces polymers substantially as high in molecular weight as those produced by argon-stripping.

TABLE VI-1

| Run No. | AA g | Water g$^{(a)}$ | AI$^{(b)}$ | Degasification$^{(c)}$ | Alcohol Oxidase μl$^{(d)}$ | Ethanol μl |
| --- | --- | --- | --- | --- | --- | --- |
| 42 | 20 | 180 | 0.04 | — | — | — |
| 43 | 20 | 180 | 0.04 | Argon | — | — |

TABLE VI-1-continued

| Run No. | AA g | Water g[a] | AI[b] | Degasification[c] | Alcohol Oxidase μl[d] | Ethanol μl |
|---|---|---|---|---|---|---|
| 44 | 20 | 180 | 0.04 | — | 25 | 100 |

[a]Distilled water.
[b]2,2'-azobisisobutyronitrile.
[c]By bubbling the gas through the reactor contents. Samples not degassed were "capped" with argon to have an oxygen-free head space.
[d]Alcohol oxidase derived from the yeast Pichia pastoris (Provesta Corporation, Bartlesville, OK).

EXAMPLE VII

In Runs 45-48, sodium 2-acrylamido-2-methyl-1-propanesulfonate (SA) was homopolymerized to compare results using sodium bisulfite versus results obtained using only degassing. Polymerization was conducted at room temperature. All samples were degassed for 15 minutes after addition of reagents. Two of the Runs (47, 48) further were treated with sodium bisulfite. Runs 45-48 were made in order to compare the polymers obtained with and without sodium bisulfite so as to determine the effect of the inorganic bisulfite on polymer character. TABLE VII-1 sets forth the identity and amounts of reagents employed in Runs 45-48.

TABLE VII-1

| Run No. | SA g[a] | Water g[b] | SNSW g[c] | AI g[d] | Sodium Bisulfite g |
|---|---|---|---|---|---|
| 45 | 132 | 88 | — | 0.07 | — |
| 46 | 132 | — | 88 | 0.07 | — |
| 47 | 132 | 88 | — | 0.07 | 0.70 |
| 48 | 132 | 88 | — | 0.07 | 0.70 |

[a]The weight shown is for a 50% by wt. solution of SA in water.
[b]Distilled water, gram.
[c]Synthetic North Sea Water. See Example I.
[d]Same initiator as in Example I.

In Runs 47 and 48 polymerization actually began before the degassing. After polymerizations were complete, samples of each polymer were evaluated for relative viscosity and inherent viscosity at 0.10 weight percent polymer in SNSW, with the results of such evaluations being set forth in TABLE VII-2:

TABLE VII-2

| Run No. | Relative Viscosity | Inherent Viscosity |
|---|---|---|
| 45 | 1.87 | 6.26 |
| 46 | 1.92 | 6.50 |
| 47 | 1.36 | 3.06 |
| 48 | 1.05 | 0.48 |

It is clear that the use of the inorganic sulfite reducing agent greatly decreased the resulting polymer viscosity, and therefore, that the presence of the bisulfite adversely affects the polymer character.

EXAMPLE VIII

Further runs 49-57 were made to prepare homopolymers or copolymers of one or more of acrylamide (AM), N-vinylpyrrolidone (VP), and/or sodium 2-acrylamido-2-methyl-1 propanesulfonate (SA). All polymerization conditions essentially were the same, generally involving charging the reagents, exchanging (purging) the air space (head space) of each container above the polymerization admixture with nitrogen, capping, and polymerizing at room temperature. The polymerization admixtures of Runs 49 through 55 were purged (sparged) for 15 minutes, and those of Runs 55 and 57 for six minutes. Otherwise, polymerization conditions were essentially the same for each of Runs 49-57. Runs 50, 51, 53, 54, 56, and 57 contained, in addition to the initiator, sodium bisulfite in indicated amounts. These Runs were made in order to determine the effects of the presence of sodium bisulfite on oil field type polymers. TABLE VIII-1 sets forth the identity and amounts of reagents employed in Runs 49-57.

TABLE VIII-1

| Run No. | VP g | AM g | SA g[a] | Water g[b] | AI g[c] | Sodium Bisulfite g |
|---|---|---|---|---|---|---|
| 49 | 36 | 24 | — | 130 | 10 | 0 |
| 50 | 36 | 24 | — | 130 | 10 | 0.06 |
| 51 | 36 | 24 | — | 130 | 10 | 0.6 |
| 52 | 18 | 9 | 66 | 97 | 10 | 0 |
| 53 | 18 | 9 | 66 | 97 | 10 | 0.06 |
| 54 | 18 | 9 | 66 | 97 | 10 | 0.6 |
| 55 | — | 60 | — | 130 | 10 | 0 |
| 56 | — | 60 | — | 130 | 10 | 0.06 |
| 57 | — | 60 | — | 130 | 10 | 0.60 |

[a]Charged as 50% by wt. solution in water.
[b]Distilled water.
[c]2,2-Azobis (N,N'-dimethyleneisobutyramidine) dihydrochloride charged as a 0.6 wt. % solution in distilled water. The weight shown is for the initiator solution.

Samples of each of the resulting polymers from Runs 49-57 then were evaluated for relative and inherent viscosity at 0.10 weight percent polymer in Substitute Ocean Water (SOW). Substitute Ocean Water was prepared by dissolving 36.032 of commercially available "sea salt" from Lake Products Co. Ballwin, Mo. in deionized water to make one liter of solution. The results of these viscosity evaluations are set forth in TABLE VIII-2.

TABLE VIII-2

| Sample | Relative Viscosity | Inherent Viscosity |
|---|---|---|
| 49 | 2.00 | 6.95 |
| 50 | 1.99 | 6.87 |
| 51 | 1.90 | 6.44 |
| 52 | 2.07 | 7.26 |
| 53 | 2.11 | 7.46 |
| 54 | 2.05 | 7.17 |
| 55 | 2.42 | 8.84 |
| 56 | 1.67 | 5.10 |
| 57 | 1.06 | 0.59 |

Runs 49, 50, and 51 each prepared a copolymer of VP/AM. Run 49 employed no added sodium bisulfite, while Runs 50 and 51 did employ sodium bisulfite, with Run 51 using ten times the amount of sodium bisulfite used in Run 50. It is apparent that the inherent viscosity of the resulting polymers of Runs 49-51 decreased progressively with increasing amounts of the bisulfite.

Runs 52, 53, and 54, each prepared a terpolymer of VP/AM/SA, again with no bisulfite, with bisulfite, and with ten times the amount of bisulfite, respectively. Inherent viscosity of the resulting polymers of Runs 52-54 showed no particular effects from the bisulfite.

Runs 55, 56, and 57 each prepared a homopolymer of AM. Again the same sequence of bisulfite was employed, none, an amount, and ten times the amount, respectively. The results were dramatic in inherent viscosity, the bisulfite treatment polymerizations resulting in a poorer polymer as far as inherent viscosity was concerned at one amount, and an almost unusable material in the larger amount.

These data show that the presence of the bisulfite does have an effect, that such effect does depend to some extent on the type of polymer employed, and that, in general, the effect, as far as inherent viscosity is concerned, can range from unpredictable to progressive deterioration to drastic decreases.

EXAMPLE IX

Runs 58–66 were made to prepare homopolymers and copolymers involving one or more of VP, AM, and SA, using in each Run substantially the same amount of initiator. Runs 58, 61, and 64 employed no bisulfite, while Runs 59, 60, 62, 63, 65, and 66 included the use of bisulfite, but all of Runs 58–66 included alcohol oxidase/ethanol as an oxygen scavenging system. The purpose of Runs 58–66 was to study the effects of the presence of the sodium bisulfite disclosed in the prior art on various polymers.

In general, in each of Runs 58–66, the various reagents were charged to the reaction container, the space above the solution purged for uniformity with nitrogen, the containers capped, and polymerization then allowed to proceed at room temperature. TABLE IX-1 sets forth the identity and amounts of reagents employed and the results obtained in Runs 58–66.

After polymerization, a portion of the polymer of each of Runs 58–66 was then evaluated for relative viscosity and inherent viscosity determination as in Example VIII. The results of these viscosity evaluations are set forth in TABLE IX-2.

TABLE IX-1

| Run No. | VP g | AM g | SA g$^{(a)}$ | Distilled Water g | Initiator g$^{(b)}$ | Sodium Bilsulfite g | Ethanol μL | Enzyme μl$^{(d)}$ |
|---|---|---|---|---|---|---|---|---|
| 58 | 36 | 24 | — | 130 | 10 | 0 | 100 | 50 |
| 59 | 36 | 24 | — | 130 | 10 | 0.06 | 100 | 50 |
| 60 | 36 | 24 | — | 130 | 10 | 0.60 | 100 | 50 |
| 61 | 18 | 9 | 66 | 97 | 10 | 0 | 100 | 50 |
| 62 | 18 | 9 | 66 | 97 | 10 | 0.06 | 100 | 50 |
| 63 | 18 | 9 | 66 | 97 | 10 | 0.60 | 100 | 50 |
| 64 | — | 60 | — | 130 | 10 | 0 | 100 | 50 |
| 65 | — | 60 | — | 130 | 10 | 0.06 | 100 | 50 |
| 66 | — | 60 | — | 130 | 10 | 0.60 | 100 | 50 |

$^{(a)}$Charged as 50% by wt. solution in water.
$^{(b)}$Same initiator solution as used in Example VIII.
$^{(c)}$Alcohol oxidase enzyme derived from the yeast *Pichia pastoris* (Provesta Corporation, Bartlesville, OK).

TABLE IX-2

| Sample No. | Relative Viscosity | Inherent Viscosity |
|---|---|---|
| 58 | 1.93 | 6.57 |
| 59 | 2.01 | 6.98 |
| 60 | 1.87 | 6.26 |
| 61 | 1.96 | 6.72 |
| 62 | 2.07 | 7.27 |
| 63 | 2.05 | 7.19 |
| 64 | 1.99 | 6.86 |
| 65 | 1.53 | 4.28 |
| 66 | 1.05 | 0.53 |

Runs 58, 59, and 60 each prepared a copolymer of VP/AM. It appears that the presence of the bisulfite was not deleterious to the resulting inherent viscosity.

Runs 61, 62, and 63 each prepared a terpolymer of VP/AM/SA. Here, the presence of a bisulfite appeared not to be deleterious.

Runs 64, 65, and 66 each prepared a homopolymer of AM. The effects of the bisulfite were deleterious, in a drastic fashion, as can be observed above.

EXAMPLE X

Runs 67–78 were made to again study the effects of a bisulfite on resulting polymer viscosity when the air space above each sample in the container was not purged, and the polymerization admixture itself was not treated with our oxygen scavenging system. In general, in each of Runs 67–78, all reagents were added to the container, and polymerization was allowed to proceed at room temperature. TABLE X-1 sets forth the identity and amounts of reagents employed and the results obtained in Runs 67–78.

TABLE X-1

| Run No. | VP g | AM g | SA g$^{(a)}$ | Distilled Water | AI g$^{(b)}$ | Sodium Bilsulfite g | Induction Period |
|---|---|---|---|---|---|---|---|
| 67 | 36 | 24 | — | 130 | 10 | 0 | — |
| 68 | 36 | 24 | — | 130 | 10 | 0.06 | no polymerization |
| 69 | 36 | 24 | — | 130 | 10 | 0.60 | — |
| 70 | 36 | 24 | — | 130 | 10 | 3.00 | — |
| 71 | 18 | 9 | 66 | 97 | 10 | 0 | — |
| 72 | 18 | 9 | 66 | 97 | 10 | 0.06 | — |
| 73 | 18 | 9 | 66 | 97 | 10 | 0.60 | — |
| 74 | 18 | 9 | 66 | 97 | 10 | 3.00 | — |
| 75 | — | 60 | — | 130 | 10 | 0 | no polymerization |
| 76 | — | 60 | — | 130 | 10 | 0.06 | 1 hour |
| 77 | — | 60 | — | 130 | 10 | 0.60 | — |
| 78 | — | 60 | — | 130 | 10 | 3.00 | — |

$^{(a)}$Charged as 50% by wt. solution in water.
$^{(b)}$Same initiator solution as used in Example VIII.

Runs 67 through 75, inclusive, either did not polymerize or only polymerized in part even over several days. Runs 76 through 78 did polymerize within a day or two.

A portion of the product of each of Runs 67–78 was obtained in order to determine inherent viscosity at 0.10 weight percent polymer in SOW, with the results of these inherent viscosity determinations being set forth in TABLE X-2.

TABLE X-2

| Run No. | Inherent Viscosity |
|---|---|
| 67 | 5.14 |
| 68 | 0.07 |
| 69 | 7.32 |
| 70 | 3.83 |
| 71 | 7.64 |
| 72 | 8.24 |
| 73 | 7.93 |
| 74 | 4.76 |
| 75 | 0.04 |
| 76 | 6.70 |
| 77 | 1.00 |
| 78 | 0.15 |

It is clear, again, that the presence of the bisulfite in Runs 68–70, 72–74, and 76–78 produced erratic results, generally deleterious, but less apparent in Runs 72–74 when the polymer contained SA as a monomer component.

In general, the data obtained indicate that the prior art method of inert gas purging probably is the best approach, and remains so. However, in the situation described in the present application, inert gas purging is simply not available. The prior art suggests the use of sulfite-type oxygen scavenging compounds. Unfortunately, the bisulfites produced erratic and unpredictable results, usually deleterious to the polymer. These results teach against the use of chemical oxygen scavenging agents.

As previously stated, applicants have discovered that the use of our oxygen scavenging systems consistently and uniformly produce excellent results, in the face of data indicating that prior art chemical oxygen scavenging agents are undesirable.

The following summary of information compares selected runs from the several Examples above.

The following Tables compare some of the previous runs to more clearly demonstrate the effect of bisulfite ion ($HSO_3^-$) on radical-initiated room temperature polymerization to three types of polymers:

(1) VP/AM (N-vinyl-2-pyrrolidone/acrylamide)-copolymer;

(2) VP/AM/SA (N-vinyl-2-pyrrolidone/acrylamide/2-acrylamido-2-methyl-1-propanesulfonic acid, sodium salt)terpolymer; and (3) AM (acrylamide) homopolymer.

The runs were conducted under three different modes of oxygen removal;

A) inert gas ($N_2$) purging of the liquid phase prior to polymerization;

B) charging ethanol plus alcohol oxidase to the polymerization mixture (and $N_2$ purging of the reactor vapor space;) and C) use of bisulfite alone as a chemical $O_2$ scavenger.

Conditions A) and C) are prior art techniques while condition B) is the inventive procedure.

The radical initiator used in these runs, identified as V 56 and currently designated VA-044 by the supplier, is 2,2-azobis(N,N'-dimethyleneisobutyramidine)dihydrochloride.

Inherent viscosity measurements of 0.10 weight percent polymer solution in SOW (synthetic ocean water) are used to compare polymer molecular weights.

TABLE XI

| | VP/AM Copolymer[a] | | |
|---|---|---|---|
| Run No. | $O_2$ Removal Mode | $NaHSO_3$, phm | Inherent Viscosity |
| 49 | A[b] | 0 | 6.95 |
| 58 | B[c] | 0 | 6.57 |
| 67 | C[d] | 0 | 5.14 |
| 68 | C[d] | 0.1 | 0.07 |
| 69 | C[d] | 1.0 | 7.32 |
| 70 | C[d] | 5.0 | 3.83 |
| 50 | A[b] | 0.1 | 6.87 |
| 51 | A[b] | 1.0 | 6.44 |
| 59 | B[c] | 0.1 | 6.98 |
| 60 | B[c] | 1.0 | 6.26 |

[a]VP/AM (N-vinyl-2-pyrrolidone/acrylamide) copolymer.
[b]Polymerization for 4 days.
[c]Polymerization for 3 days.
[d]Polymerization for 5 days. Reaction mixture appearance indicated incomplete polymerization.

Comparison of inherent viscosity results for Runs 49, 58, and 67 shown in TABLE XI, indicate that our inventive oxygen scavenging system B was not quite as effective as prior art mode A, but that both modes were much better than no treatment at all in Run 67.

Even though Run 69 did show a high inherent viscosity value, Runs 68, 69, and 70, appeared to be erratic in terms of slow incomplete polymerization.

The combination of bisulfite with mode A caused a slight decrease in inherent viscosity, while with mode B an increase was observed at 0.1 phm but a slight decrease at 1.0 phm.

TABLE XII

| | AM Homopolymer[i] | | |
|---|---|---|---|
| Run No. | $O_2$ Removal Mode | $NaHSO_3$, phm | Inherent Viscosity |
| 55 | A[j] | 0 | 8.84 |
| 64 | B[k] | 0 | 6.86 |
| 75 | C[l] | 0 | 0.04 |
| 76 | C[l] | 0.1 | 6.70 |
| 77 | C[l] | 1.0 | 1.00 |
| 78 | C[l] | 5.0 | 0.15 |
| 56 | A[j] | 0.1 | 5.10 |
| 57 | A[j] | 1.0 | 0.59 |
| 65 | B[k] | 0.1 | 4.28 |
| 66 | B[k] | 1.0 | 0.53 |

[i]AM (acrylamide) homopolymer.
[j]Polymerization for 4 days.
[k]Polymerization for 3 days.
[l]Polymerization for 5 days.

Again, in TABLE XII, a comparison of inherent viscosity results for Runs 55, 64, and 75 indicate that the inventive oxygen removal mode B was not as effective as prior art mode A, while Run 75 (no treatment) showed very little polymerization at all. In Runs 76, 77, and 78, there seemed to be a small optimum amount of bisulfite effective in removing oxygen (Run 76). Larger amounts of bisulfite caused a drastic decrease in inherent viscosity (Runs 77 and 78). Used in combination with modes A or B, even a small amount of bisulfite caused a drop in inherent viscosity (Runs 56, 57, 65, and 66).

In summary, the results in Tables XI and XII demonstrate that our inventive oxygen removal mode B was not quite as effective as the prior art nitrogen purging mode A, but that our inventive mode clearly was far better than the use of a prior art inorganic chemical bisulfite because of erratic results with the latter mode C.

The disclosure, including data, has illustrated the value and effectiveness of our invention. The Examples, the knowledge and background of the field of the invention, and the general principles of chemistry and of other applicable sciences, have formed the bases from which the broad descriptions of our invention, including the ranges of conditions and the generic groups of operant components, have been developed, and have formed the bases for our claims here appended.

That which is claimed:

1. A process for polymerization which comprises admixing at least one water-soluble polymerizable vinyl monomer and a water-soluble free-radical initiator, water as polymerization solvent, and an oxygen-scavenging treatment comprising at least one oxidase, at least one substrate therefor, optionally with catalase, in an amount sufficient and effective to deoxygenate the polymerization admixture, and wherein said oxidase and substrate are selected from the pairs selected from the following groups:

| Oxidase | Substrate |
|---|---|
| tyrosinase | phenols and catechols |
| aldehyde oxidase | aldehydes and purines |

-continued

| Oxidase | Substrate |
| --- | --- |
| amino acid oxidase | amino acids |
| uricase | uric acid |
| glucose oxidase | glucose |
| amine oxidase | mono- and diamines |
| lipoxygenase | unsaturated fatty acids |
| ascorbic oxidase | Vitamin C |
| alcohol oxidase | ethanol | polymerizing said at least one monomer thereafter to form at least one polymer to form a concentrated high-viscosity polymer solution.

2. The process according to claim 1 wherein said at least one water-soluble polymerizable vinyl monomer is selected from the group consisting of acrylamide monomers, alone or optionally with at least one comonomer.

3. The process according to claim 1 wherein said at least one water-soluble polymerizable vinyl monomer comprises acrylamide.

4. The process according to claim 1 wherein said at least one water-soluble polymerizable vinyl monomer comprises acrylamide and N-vinylpyrrolidone.

5. The process according to claim 1 wherein said at least one water-soluble polymerizable vinyl monomer comprises acrylamide, N-vinylpyrrolidone, and sodium 2-acrylamido-2-methyl-1-propanesulfonate.

6. The process according to claim 1 wherein said at least one water-soluble polymerizable vinyl monomer comprises acrylamide, N-vinylpyrrolidone, sodium-2-acrylamido-2-methyl-1-propanesulfonate, and acrylic acid.

7. The process according to claim 1 wherein said at least one water-soluble polymerizable vinyl monomer comprises acrylamide, N-vinylpyrrolidone, sodium-2-acrylamido-2-methyl-1-propanesulfonate, and the sodium salt of acrylic acid.

8. The process according to claim 1 wherein said at least one water-soluble polymerizable vinyl monomer comprises acrylamide, N-vinylpyrrolidone, sodium-2-acrylamido-2-methyl-1-proponesulfonate acrylic acid and the sodium salt of acrylic acid.

9. The process of claim 1 wherein the oxidoreductase enzyme employed is selected from the group consisting of oxidase, monooxygenases, hydroxygenases, hydrolases, and oxygenases.

10. The process of claim 9 wherein the oxidoreductase enzyme is an oxidase.

11. A process according to claim 9 wherein the oxidase is alcohol oxidase and the substrate is ethanol.

* * * * *